US00PP31286P2

(12) United States Plant Patent
Overom

(10) Patent No.: US PP31,286 P2
(45) Date of Patent: Dec. 31, 2019

(54) CLIMBING ROSE PLANT NAMED 'OVEREDCLIMB'

(50) Latin Name: *Rosa hybrida*
Varietal Denomination: Overedclimb

(71) Applicant: The Conard-Pyle Company, West Grove, PA (US)

(72) Inventor: Julie Overom, Barnes, WI (US)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 16/350,636

(22) Filed: Dec. 13, 2018

(51) Int. Cl.
*A01H 5/02* (2018.01)
*A01H 6/74* (2018.01)

(52) U.S. Cl.
USPC ..... Plt./115
CPC ..... *A01H 6/749* (2018.05)

(58) Field of Classification Search
USPC ..... Plt./115
See application file for complete search history.

(56) References Cited

U.S. PATENT DOCUMENTS

PP19,310 P2 10/2008 Radler

*Primary Examiner* — Anne Marie Grunberg
(74) *Attorney, Agent, or Firm* — Buchanan Ingersoll & Rooney PC

(57) ABSTRACT

A new and distinct variety of Climbing rose plant, herein referred to by its cultivar name, 'Overedclimb', is provided which forms abundantly on a substantially continuous basis attractive, cup shaped deep red colored blossoms. Attractive, semi-glossy, medium green foliage is formed, which contrasts beautifully with the blossoms. The vegetation is vigorous and the growth habit is very bushy and climbing. The new variety is well suited for proving attractive ornamentation in the landscape.

1 Drawing Sheet

Botanical/commercial classification: Latin name—*Rosa hybrida.*

Common name—Climbing Rose Plant.

Varietal Denomination—'Overedclimb'.

SUMMARY OF THE INVENTION

The new variety of *Rosa hybrida* climbing rose plant was created during July 2006 in Lake Nebagamon, Wis., U.S.A., by artificial pollination wherein two parents were crossed which previously had been studied in the hope that they would contribute the desired characteristics. The female parent (i.e., the seed parent) was an unnamed seedling (non-patented). The male parent (i.e., the pollen parent) was an unnamed seedling (non-patented).

The parentage of the new variety can be summarized as follows:

unnamed seedling x unnamed seedling

The seeds resulting from the above pollination were sown and small plants were obtained which were physically and biologically different from each other. Selective study resulted in the identification of a single plant of the new variety.

It was found that the new variety of climbing rose plant of the present invention possesses the following combination of characteristics:

(a) forms attractive, cup shaped, deep red colored blossoms abundantly and substantially continuously, (b) exhibits a very bushy and climbing growth habit, (c) forms vigorous vegetation, (d) provides attractive ornamental semi-glossy, medium green foliage, and (e) exhibits very good disease resistance.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the unnamed seedling female parent (i.e., the seed parent) displays larger blossoms, is shorter, and exhibits less resistance to black spot and powdery mildew compared to the new variety. In addition, the unnamed seedling male parent (i.e., the pollen parent) provides a less attractive habit compared to the new variety. Moreover, the new variety can be readily distinguished from other similar non-parental varieties. For example, the 'Radwin' variety (U.S. Plant Pat. No. 19,310) displays larger blossom size compared to the new variety.

The new variety has been found to undergo asexual propagation in Wasco, Calif. by a number of routes, including vegetative cuttings. Asexual propagation by vegetative cuttings in Wasco, Calif. has shown that the characteristics of the new variety are stable and are strictly transmissible by such asexual propagation from one generation to another. Accordingly, the new variety undergoes asexual propagation in a true-to-type manner.

The new variety has been named 'Overedclimb'.

BRIEF DESCRIPTION OF THE PHOTOGRAPH

The accompanying photograph of FIG. 1 shows as nearly true as it is reasonably possible to make the same, in a color illustration of this character, a typical specimen of the new variety. The rose plant of the new variety was approximately three years of age and was observed during June 2017 while growing on its own roots and growing outdoors at Cochranville, Pa., U.S.A.

FIG. 1 illustrates a specimen the plant with blossoms at varying stages of opening.

DETAILED BOTANICAL DESCRIPTION

The chart used in the identification of the colors is that of The Royal Horticultural Society (R.H.S. Colour Chart, 2015 edition), London, England. The terminology which precedes reference to the chart has been added to indicate the corresponding color in more common terms. The description is based on the observation of two-year-old specimens of the new variety during July while growing on their own roots and growing in a three-gallon containers at Cochranville, Pa., U.S.A..

Class: Climbing rose plant.

Plant:

*Habit.*—Very busy and climbing.

*Height.*—Approximately 50.0 cm from the top of the soil plane.

*Width.*—Approximately 65.0 to 70.0 cm on average.

Branches:

*Color.*—Young stems: commonly near Yellow-Green Group 144A mixed with near Greyed-Red Group 181A. — old wood: commonly near Yellow-Green Group 144A.

*Length.*—Main stems: approximately 60.0 to 70.0 cm on average. — secondary stems: approximately 25.0 cm on average.

*Thorns.*—Young thorns: length is approximately 6.0 mm on average, width is approximately 4.0 mm at point of attachment, and color is commonly near Greyed-Orange Group 165A. — old thorns: length is approximately 1.0 cm on average, width is approximately 7.0 mm on average, and color is commonly near Brown Group 200A.

Foliage:

*General appearance.*—Medium green with a semi-glossy aspect.

*Number of leaflets.*—3, 5, and 7.

5-*Leaflet leaf.*—Length: approximately 9.0 cm on average. — width: approximately 6.0 cm on average.

*Young foliage.*—Upper and under surfaces color: commonly near Green Group 137A.

*Old foliage.*—Upper surface color: commonly near Green Group 137A. — under surface color: commonly near Green Group 137C.

Leaflets:

*Shape.*—Ovate.

*Texture.*—Upper and under surface is smooth.

*Terminal leaflet.*—Length: approximately 3.0 cm on average. — width: approximately 2.5 cm on average.

*Lower leaflet.*—Length: approximately 2.5 cm on average. — width: approximately 2.0 cm on average.

*Leaf margin.*—Serrate.

*Petiole.*—Upper surface: color is commonly near Green Group 143B and texture is smooth. — under surface: color is commonly near Green Group 143C and texture is glandular with some small prickles.

*Rachis.*—Color of upper surface: commonly near Green Group 143B. — color of under surface: commonly near Green Group 143C.

*Stipules.*—Margin: entire to erose. — length: approximately 1.8 cm on average. — width: approximately 2.0 mm on average. color of upper surface: commonly near Green Group 143B with some mixing of near Greyed-Orange Group 176A particularly close to the innermost portion. — color of lower surface: commonly near Green Group 143C.

Inflorescence:

*Number of flowers.*—Generally about 50 blooms on average on a plant at once.

*Number of blooms per stem.*—Generally between 1 to 6 blooms per stem.

*Bud.*—Shape: ovoid. — length: approximately 2.0 cm on average. — width: approximately 1.5 cm on average. — color when opening: commonly near Red Group 45C.

*Sepals.*—Number: commonly 5 on average. — length: approximately 3.0 cm on average. — width: approximately near 1.1 cm on average. — margin: entire with extensions on two or three sepals measuring approximately 5.0 mm in length on average and 1.0 mm in width on average. — upper surface color and texture: commonly near Yellow-Green Group 144A; covered in short pubescence. — under surface color and texture: commonly near Yellow-Green Group 144C; puberulent.

*Receptacle.*—Achenes stand on the bottom and wall. — color: commonly near Yellow-Green Group 144A. — diameter: approximately 7.0 mm on average. — surface texture: smooth. — shape: round.

*Peduncle.*—Length: approximately 3.0 cm on average. — diameter: approximately 1.0 mm on average. — surface texture: sparely covered in short, flexible thorns that measure less than 2.0 mm in length. — color: commonly near Yellow-Green Group 144B.

*Flower.*—Diameter: approximately 4.5 cm on average. — height: approximately 3.0 cm on average. — duration: flower is on the plant approximately 5 days. — shape: cup. — form: double. — number of petals under normal conditions: approximately 22 petals on average. — shape of the petal: overall: broadly obovate. base: cuneate. apex: slightly cuspidate. — petal length: approximately 2.3 cm on average. — petal width: approximately 2.2 cm on average. — petal margin: entire. — petal drop: good. — fragrance: very slight. — color when opening begins: upper surface: commonly near White Group 155A at the point of attachment, transitions to near Red Group 53A. under surface: commonly near White Group 155A at the point of attachment, transitions to near Red-Purple Group 61C. — color at end of blooming: upper surface: at the point of attachment commonly near White Group NN155A blending to Red-Purple Group 63B towards the apex. under surface: at the point of attachment commonly near White Group 155B blending to Red Group 55B towards the apex.

*Stamen.*—Number is approximately 100 on average. — anthers: number is approximately 100 on average and coloration is commonly near Greyed-Orange Group N166B. — filaments: length is approximately 1.0 cm on average and coloration is commonly near Green-Yellow Group 1A fading to Yellow-Orange Group 22A toward the apex.

*Pistils.*—Arrangement is separate and free; number is approximately 33 on average. — styles: length is approximately 5.0 mm on average and coloration is commonly near Yellow Group 13C. — stigmas: diameter is approximately 1.0 mm on average and coloration is commonly near Yellow Group 13A.

*Pollen.*—Color is commonly near Yellow-Orange Group 19A and a moderate amount is present.

*Hips.*—Amount is minimally produced; immature color is commonly near Yellow-Green Group 144C; mature color is commonly near Orange Group N25A; shape is spherical to slightly oval; texture is glabrous; length is approximately 11.0 mm to 15.0 mm; and width is approximately 9.0 mm to 11.0 mm.

Development:

*Vegetation.*—Vigorous and strong.

*Hardiness.*—Hardy to USDA zone 4.

*Blooming.*—Abundant and substantially continuous from spring through frost.

*Resistance to disease.*—Very good resistance for black spot and powdery mildew.

The new 'Overedclimb' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of Climbing Rose plant characterized by the following combination of characteristics:

(a) forms attractive, cup shaped, deep red colored blossoms abundantly and substantially continuously, (b) exhibits a very bushy and climbing growth habit, (c) forms vigorous vegetation, (d) provides attractive ornamental semi-glossy, medium green foliage, and (e) exhibits very good disease resistance; substantially as herein shown and described.

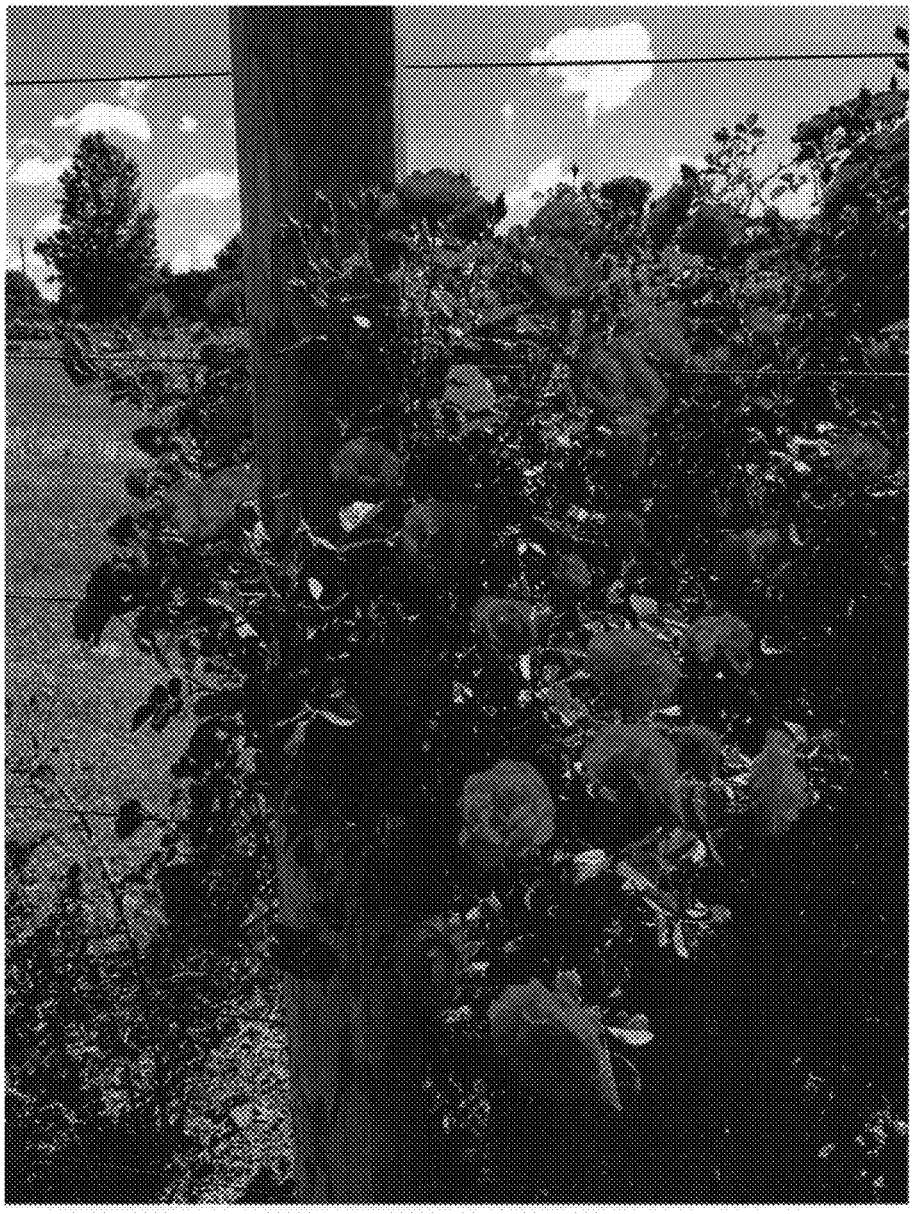

* * * * *